United States Patent
Murday

(10) Patent No.: US 11,311,494 B2
(45) Date of Patent: Apr. 26, 2022

(54) COLD SORE TREATMENT FORMULATION AND RELATED METHOD OF APPLICATION-LIQUID PATCH FOR TREATMENT OF VIRAL LESIONS

(71) Applicant: Adam Mark Murday, Barrie (CA)

(72) Inventor: Adam Mark Murday, Barrie (CA)

(73) Assignee: Adam Mark Murday, Midland (CA)

( * ) Notice: Subject to any disclaimer, the term of this patent is extended or adjusted under 35 U.S.C. 154(b) by 0 days.

(21) Appl. No.: 16/871,364

(22) Filed: May 11, 2020

(65) Prior Publication Data
US 2020/0360298 A1    Nov. 19, 2020

Related U.S. Application Data

(60) Provisional application No. 62/846,810, filed on May 13, 2019.

(51) Int. Cl.
| | |
|---|---|
| *A61K 9/70* | (2006.01) |
| *A61K 47/46* | (2006.01) |
| *A61K 47/38* | (2006.01) |
| *A61K 47/08* | (2006.01) |
| *A61K 47/10* | (2017.01) |
| *A61K 47/14* | (2017.01) |
| *A61K 31/14* | (2006.01) |
| *A61K 31/198* | (2006.01) |
| *A61K 31/519* | (2006.01) |
| *A61K 33/06* | (2006.01) |
| *A61K 33/30* | (2006.01) |
| *A61L 26/00* | (2006.01) |
| *A61K 31/045* | (2006.01) |

(52) U.S. Cl.
CPC .......... *A61K 9/7015* (2013.01); *A61K 31/045* (2013.01); *A61K 31/14* (2013.01); *A61K 31/198* (2013.01); *A61K 31/519* (2013.01); *A61K 33/06* (2013.01); *A61K 33/30* (2013.01); *A61K 47/08* (2013.01); *A61K 47/10* (2013.01); *A61K 47/14* (2013.01); *A61K 47/38* (2013.01); *A61K 47/46* (2013.01); *A61L 26/0004* (2013.01); *A61L 26/0023* (2013.01); *A61L 26/0057* (2013.01); *A61L 26/0066* (2013.01); *A61L 2300/404* (2013.01)

(58) Field of Classification Search
CPC ...... A61K 9/7015; A61K 47/38; A61K 31/14; A61L 26/0066; A61L 2300/404
See application file for complete search history.

(56) References Cited

U.S. PATENT DOCUMENTS

| | | | | |
|---|---|---|---|---|
| 2004/0071757 | A1* | 4/2004 | Rolf | A61K 9/7061 424/443 |
| 2006/0115522 | A1* | 6/2006 | Lulla | A61K 31/445 514/183 |
| 2006/0269592 | A1* | 11/2006 | Hart | A61F 13/023 424/448 |
| 2007/0026056 | A1* | 2/2007 | Rolf | A61F 13/023 424/769 |
| 2009/0258841 | A1* | 10/2009 | Murphy | A61P 17/08 514/125 |

* cited by examiner

Primary Examiner — Andrew S Rosenthal

(57) ABSTRACT

A formulation of a discrete liquid patch for the treatment of cold sores or viral lesions, including a combination of the adhesive layer and an active compound/ingredient such as antiviral agents, and/or amino acids, and/or minerals/vitamins. The adhesive layer of the discrete patch is substantially free of hydrocolloid particles. The adhesive layer does not include any backing layer to maintain the compliance of the patch with a thickness ranging from 5 microns to 1,300 microns. Wherein, the discrete patch of the invention is configured to apply to a viral lesion to maintain in contact therewith for a time effective to substantially complete re-epithelialization of the lesion.

14 Claims, No Drawings

COLD SORE TREATMENT FORMULATION AND RELATED METHOD OF APPLICATION-LIQUID PATCH FOR TREATMENT OF VIRAL LESIONS

CROSS-REFERENCE TO RELATED APPLICATIONS

The present application is entitled to priority under 35 U.S.C § 119(e), to U.S. Provisional Application No. 62/846,810, filed May 13, 2019.

BACKGROUND OF THE INVENTION

Field of the Invention

The present invention relates to a formulation of the liquid discreet patch for the treatment of the viral lesions cause by herpes simplex virus infection.

Description of the Related Art

Herpes Labialis, commonly known as cold sores, is a type of infection by the herpes simplex virus (HSV) that affects primarily the lip. HSV-1 and 2 infections are characterized by a high frequency of recurrence and extremely contagious. Herpes Labialis, causes physical pain and discomfort and can also be disfiguring, especially in those patients with a high frequency of recurrence. Those afflicted with the virus often tend to be embarrassed by the appearance of the lesions.

The global seroprevalence of HSV-1 in adults is currently 70-80%, resulting in 400 million or more cold sores per annum. 80-90% of the adult population and 40-50% of adolescent populations in the United States have been exposed to the HSV-1 Virus and Approximately 40% of the afflicted population has had a cold sore at one time or another. Furthermore, the majority of people who have had cold sores, will most commonly suffer reoccurring outbreaks. To that point, more than 50 million adults in the United States have 2 or more outbreaks per year. A typical outbreak will generally regress within 7-10 days, with complete healing in 12-14 days, although a scar or erythema may persist.

The uncomfortable and sensitive lesions of the Herpes Labialis are painful while touching and interferes with patients' daily routines such as drinking and eating. Additionally, the unsightly nature of the lesions coupled with the discomfort results in patients being embarrassed. Although 90% of the population is exposed to the virus in their lifetime, there is a social element of antipathy to the virus that adds to this embarrassment.

Creating a barrier or a layer on the surface of the lesion protects from outside influences like, bacteria, dirt and even physical agitation helps to reduce the sensitivity to the affected area and improves the patient's ability to perform daily routines. The best method to create the layer on the surface of the lesion is the application of the patch. It is most common over-the-counter (OTC) solution for the Herpes Labialis. Patient's often have trouble restraining themselves from touching the lesion, which can result in spread of the infection, and/or exacerbating the lesion and increasing healing times. Patches create a preventative barrier and can eliminate/reduce this influence with less sensation experience.

The formulation or composition of the patch is an essential part to provide a lighter and more flexible/stable patch that is less prominent and still provides significant healing and usage time properties. All of the existing commercial applications include a formulation that consists of an adhesive layer and a backing layer. Most commonly, non-medicated and containing a hydrocolloid layer for wicking moisture (a hydrocolloid ingredient combines with moisture produced by the lesion and it turns into a gel like substance). Some commercial patches are also a non-hydrocolloid patch composition. Abreva is the most well-known non-hydrocolloid base and is additionally a non-medicated patch. Common hydrocolloidal patches include Compeed and Polysporin, both non-medicated.

Canadian Patent No. CA 2609259 discloses a hydrocolloid base patch, which includes a backing layer for treating Herpes Labialis. US Patent application No. 20070026056A1 also discloses a backing of a flexible sheet of water insoluble material.

Hydrocolloid base patch formulations with or without active ingredient leads to become unsightly as the lesion underneath produces a buildup of organic material in a gel-like substance, which causes the patch to become thicker and often destabilizes the adhesion of the patch and results in to the more visible patch.

Non-Hydrocolloid base patch formulations without active ingredients would not experience the gelling of organic materials but they do not effectively manage the moisture produced by the lesion. The moisture builds up beneath the patch and destabilizes the adhesive, separating he patch from the skin. It becomes more visible and uncomfortable, and likewise a hotspot for activity and increased bacterial load. Additional lack of active-ingredients slows down the healing process. The application of the hydrocolloid base and non-hydrocolloid base patches is not easy and interferes with the physical appearance and can agitate the area further, which may increase the infection at the affected area.

Therefore, a need still exists for a lighter and more flexible/stable patch that is less prominent and still provides significant healing and usage time properties while including a medicated active ingredient, without triggering more infection. The present invention includes formulation of an easy to apply translucent liquid patch with improve healing time and reduce irritation.

SUMMARY

The present invention provides a medicated translucent liquid discreet patch for the treatment of cold sores/viral lesions that provides lighter and more flexible/stable patch with significant healing and usage time properties without triggering more infection.

The present invention includes formulation of a liquid discreet patch comprising of a translucent liquid adhesive, at least one active ingredient, a non-active ingredient, and an optional anti-septic compound. The translucent liquid adhesive is composed of alcoholic base, which includes the non-active ingredient. Whereas, the liquid discreet patch does not require additional backing layer.

In accordance with the invention, the formulation of a liquid discreet patch further includes preparation of formulation by mixing one or more non-active ingredients at specific temperature and mixing condition to form a translucent liquid adhesive. Other ingredients such as the active-ingredients and the anti-septic compound can be mixed separately at specific temperature and mixing condition to form a translucent liquid. Furthermore, the two separate mixture combine to form the liquid discreet patch formulation.

A preferred embodiment of the invention comprises the active ingredient selected from group consist of anti-viral compounds, amino acids and vitamins such as Docosanol, L-lysine, Acyclovir, Penciclovir, Zinc and Magnesium. Whereas, at least one active ingredient can be combined with the alcohol base translucent liquid adhesive to form translucent liquid discreet patch. The anti-septic compounds such as Benzalkonium Chloride and Benzethonium Chloride can be mix with the liquid discreet patch formulation.

According to another aspect of the invention, the liquid discreet patch can be use in treatment of viral lesion or cold sore by applying as a liquid on top of a part of the skin/anatomical lesion surface, principally the lips and/or facial area. Once the patch is air dried, it forms a protective translucent film barrier to prevent additional spread of the virus and contamination from microorganisms and fine particles.

According to another aspect of the invention, the translucent nature of the liquid patch reduces physical appearance of lesions. Furthermore, the nature of the patch allows for the use of a facial makeup without negatively effecting the properties of the patch. The patch is maintained in contact with the cold sore/lesion to improve healing time, reduce the spread of the virus and reduce time to complete re-epithelization, as compared to an untreated cold sore/viral outbreak.

The foregoing and other features of the invention are hereinafter fully described and particularly pointed out in the claims, the following description setting forth in detail one or more illustrative embodiments of the invention, such being indicative, however, of but one or a few of the various ways in which the principles of the invention may be employed.

DETAILED DESCRIPTION

The present invention relates to a composition/formulation for treatment of cold sores/viral lesions. It intended to improve healing times, reduce discomfort and prevent secondary/spread of infection.

More specifically, the present invention relates to formulation of the liquid discreet patch comprising of a translucent liquid adhesive, at least one active ingredient, at least one non-active ingredient, and an anti-septic compound. The translucent liquid adhesive is composed of alcoholic base, which includes the non-active ingredient. Whereas, the liquid discreet patch does not require additional backing layer.

According to a preferred embodiment, the formulation comprises, the translucent liquid adhesive, which is composed of an alcohol base due to the anti-septic qualities. However, for the purpose of active ingredient delivery, hydrophilic and silicon bases can also be use. The alcohol base composition of the translucent liquid adhesive further includes the at least one non-active ingredient is selected from the group consisting of Nitrocellulose, Tea Tree Oil, Camphor, Dimethyl Sulfoxide (DMSO), Amyl Acetate, Ethyl Acetate, Ethyl Alcohol and Isopropyl Alcohol. More specifically, composition comprises suitable weights of total formulation; Nitrocellulose 0% to 20%, Tea Tree Oil suitable 0% to 10%, Camphor 0% to 10%, Amyl Acetate 0% to 20%, Ethyl Acetate 0% to 30%, Ethyl Alcohol 0% to 30%, Isopropyl Alcohol 0% to 20%, Dimethyl Sulfoxide (DMSO) 0% to 45%. In certain situations, the non-active ingredients can also be combined with the active ingredients during preparation of formulation.

According to another preferred embodiment, the formulation of the present invention also contains at least one the active ingredient selected from group consisting of anti-viral, amino acids and vitamin ingredients such as Docosanol, L-lysine, Acyclovir, Penciclovir, Zinc, and Magnesium. More specifically, composition comprises suitable weights of total formulation; Docosanol 0% to 10%, L-lysine 0% to 10%, Penciclovir 0% to 5%, Acyclovir 0% to 5%, Magnesium 0% to 10% and Zinc 0% to 10%. The active ingredient can be mixed with the anti-septic compound and the non-active ingredients during preparation of formulation.

According to the present invention, the formulation of the liquid discreet patch may further include at least one additional antiseptic compound selected from the group consisting of Benzethonium Chloride and Benzalkonium Chloride. More specifically, composition comprises suitable weights of total formulation; Benzethonium Chloride 0% to 5% and Benzalkonium Chloride 0% to 5%.

According to the present invention, the liquid discreet patch can be applied on to the surface of the lesion by positioning the liquid discreet patch on to a lesion surface and maintaining contact between the liquid discreet patch with the lesion surface for at least 2 hours, but no longer than 12 hours. Subsequent patches can be applied and maintained in contact with the lesion surface, until such time as re-epithelialization of the lesion surface is completed. More specifically, the liquid discreet patch can be applied as a liquid over the affected dermal region, typically of the mouth and facial area. The liquid discreet patch is designed to dry and form a porous, translucent film barrier that allows moisture to pass through the patch and evaporate to maintain adhesion and a dry surface area. The liquid discreet patch can also help prevent the growth and spread of the virus by acting as a barrier, reducing interaction and reducing/eliminating discomfort.

In accordance with the invention, the liquid discreet patch is characterized by consisting of a single layer with absence of any additional secondary or tertiary structures or elements such as a backing layers and wound dressings. The liquid discreet patch delivery the active ingredients at the site of the cold sore outbreaks or lesions.

Accordingly, according to a preferred embodiment, the formulation of the present invention where the thickness of the liquid discreet patch is between 5 and 1300 microns to maintain translucent nature and low visibility of the patch after application on to the surface of the lesion.

According to a preferred embodiment, the liquid discreet patch can be applied to a clean surface area as soon as the afflicted identifies an oncoming outbreak and should remain in contact with the cold sore/lesion for a time up to 12 hours but no less than 2 hours. The patch can be maintained in contact with the lesion surface until re-epithelization has been completed. To achieve an effect the patch can be replaced concurrently with another patch until completion re-epithelization.

In accordance with the invention, the liquid discreet patch can be prepared by a two-step process at room temperature. The First step consists of the mixing of one or more the non-active ingredients while stirring at room temperature for about 30 minutes until it gets dissolves with mixing speed is 300-1000 rpm. The second step consist of the mixing of active ingredients and anti-septic compounds and/or non-active ingredients separately in the order determined by the formulation at room temperature with a mixing speed of 300-1000 rpm. A total mixing time is 60 minutes or until all the ingredients dissolve completely to obtained a transparent solution.

EXAMPLES

Several Examples are set forth below. The claims should not be considered to be limited to the details thereof.

Example 1

(The liquid discreet patch with Docosanol 4%)

| Components | Quantity (% w/w) |
|---|---|
| Docosanol | 4% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 8% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Docosanol (4.0 g), ethyl alcohol (15.0 g), and isopropyl alcohol (8.0 g) at room temperature with a mixing speed of 300-1000 rpm. A total mixing time including stage 1) is 60 minutes or until all the ingredients dissolve completely.

Example 2

(The liquid discreet patch with Docosanol 4% with an Anti-septic additive; Benzethonium Chloride 0.2%)

| Components | Quantity (% w/w) |
|---|---|
| Docosanol | 4% |
| Benzethonium Chloride | 0.2% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 7.8% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Docosanol (4.0 g), ethyl alcohol (15.0 g), isopropyl alcohol (7.8 g), and Benzethonium chloride (0.2 g) at room temperature with a mixing speed of 300-1000 rpm. A total mixing time including stage 1) is 60 minutes or until all the ingredients dissolve completely.

Example 3

(The liquid discreet patch with Docosanol 4% with an Anti-septic additive; Benzalkonium Chloride 0.2%)

| Components | Quantity (% w/w) |
|---|---|
| Docosanol | 4% |
| Benzalkonium Chloride | 0.2% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 7.8% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Docosanol (4.0 g), ethyl alcohol (15.0 g), isopropyl alcohol (7.8 g), and Benzalkonium Chloride (0.2 g) at room temperature with a mixing speed of 300-1000 rpm. A total mixing time including stage 1) is 60 minutes or until all the ingredients dissolve completely.

Example 4

(The liquid discreet patch with Docosanol 4% in combination with L-lysine)

| Components | Quantity (% w/w) |
|---|---|
| Docosanol | 4% |
| L-lysine | 6% |
| Tea Tree Oil | 1% |
| Nitrocellulose | 10% |
| Camphor | 1% |
| Amyl Acetate | 19% |
| Ethyl Acetate | 19% |
| Ethyl Alcohol | 10% |
| Dimethyl Sulfoxide | 30% |

Process of Preparation:
Step 1: 10.0 g of Nitrocellulose (70% dry weight: 30% isopropanol) is mixed with 30 mL of dimethyl sulfoxide while stirring at room temperature for 60 minutes or until the nitrocellulose dissolves completely in dimethyl sulfoxide; mixing speed is 300-1000 rpm
Step 2: Other ingredients are mixed and dissolved separately in the following order: L-lysine (6.0 g), ethyl alcohol (10.0 g), camphor (1.0 g), tea tree oil (1.0 g), amyl acetate (19.0 g), and ethyl acetate (19.0 g), Docosanol (4.0 g) at room temperature with a mixing speed of 300-1000 rpm. A total mixing time including stage 1) is 120 minutes or until all the ingredients dissolve completely.

Example 5

(The liquid discreet patch with L-lysine 10%)

| Components | Quantity (% w/w) |
|---|---|
| L-lysine | 10% |
| Tea Tree Oil | 1% |
| Nitrocellulose | 10% |
| Camphor | 1% |
| Amyl Acetate | 19% |

-continued

| Components | Quantity (% w/w) |
|---|---|
| Ethyl Acetate | 19% |
| Ethyl Alcohol | 10% |
| Dimethyl Sulfoxide | 30% |

Process of Preparation:
Step 1: 10.0 g of Nitrocellulose (70% dry weight: 30% isopropanol) is mixed with 30 mL of dimethyl sulfoxide while stirring at room temperature for 60 minutes or until the nitrocellulose dissolves completely in dimethyl sulfoxide; mixing speed is 300-1000 rpm
Step 2: Other ingredients are mixed and dissolved separately in the following order: L-lysine (10.0 g), ethyl alcohol (10.0 g), camphor (1.0 g), tea tree oil (1.0 g), amyl acetate (19.0 g), and ethyl acetate (19.0 g), at room temperature with a mixing speed of 300-1000 rpm. A total mixing time including stage 1) is 120 minutes or until all the ingredients dissolve completely.

Example 6

(The liquid discreet patch with Docosanol 4% in combination with L-lysine 6% and the anti-septic compound; Benzethonium Chloride 0.2%)

| Components | Quantity (% w/w) |
|---|---|
| Docosanol | 4% |
| L-lysine | 6% |
| Benzethonium Chloride | 0.2% |
| Tea Tree Oil | 1% |
| Nitrocellulose | 10% |
| Camphor | 1% |
| Amyl Acetate | 19% |
| Ethyl Acetate | 19% |
| Ethyl Alcohol | 10% |
| Dimethyl Sulfoxide | 29.8% |

Process of Preparation:
Step 1: 10.0 g of Nitrocellulose (70% dry weight: 30% isopropanol) is mixed with 29.8 mL of dimethyl sulfoxide while stirring at room temperature for 60 minutes or until the nitrocellulose dissolves completely in dimethyl sulfoxide; mixing speed is 300-1000 rpm
Step 2: Other ingredients are mixed and dissolved separately in the following order: L-lysine (6.0 g), ethyl alcohol (10.0 g), camphor (1.0 g), tea tree oil (1.0 g), amyl acetate (19.0 g), ethyl acetate (19.0 g), Docosanol (4.0 g), and Benzethonium Chloride 0.2% at room temperature with a mixing speed of 300-1000 rpm. A total mixing time including stage 1) is 120 minutes or until all the ingredients dissolve completely.

Example 7

(The liquid discreet patch with Docosanol 4% in combination with L-lysine 6% and the anti-septic compound; Benzalkonium Chloride 0.2%)

| Components | Quantity (% w/w) |
|---|---|
| Docosanol | 4% |
| L-lysine | 6% |
| Benzalkonium Chloride | 0.2% |
| Tea Tree Oil | 1% |
| Nitrocellulose | 10% |
| Camphor | 1% |
| Amyl Acetate | 19% |
| Ethyl Acetate | 19% |
| Ethyl Alcohol | 10% |
| Dimethyl Sulfoxide | 29.8% |

Process of Preparation:
Step 1: 10.0 g of Nitrocellulose (70% dry weight: 30% isopropanol) is mixed with 29.8 mL of dimethyl sulfoxide while stirring at room temperature for 60 minutes or until the nitrocellulose dissolves completely in dimethyl sulfoxide; mixing speed is 300-1000 rpm
Step 2: Other ingredients are mixed and dissolved separately in the following order: L-lysine (6.0 g), ethyl alcohol (10.0 g), camphor (1.0 g), tea tree oil (1.0 g), amyl acetate (19.0 g), ethyl acetate (19.0 g), Docosanol (4.0 g), and Benzalkonium 0.2% at room temperature with a mixing speed of 300-1000 rpm. A total mixing time including stage 1) is 120 minutes or until all the ingredients dissolve completely. A transparent solution is obtained.

Example 8

(The liquid discreet patch with Penciclovir 1%)

| Components | Quantity (% w/w) |
|---|---|
| Penciclovir | 1% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 11% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Penciclovir (1.0 g), ethyl alcohol (15.0 g), and isopropyl alcohol (11.0 g) at room temperature with a mixing speed of 300-1000 rpm. A total mixing time including stage 1) is 60 minutes or until all the ingredients dissolve completely.

Example 9

(The liquid discreet patch with Penciclovir 1% with an antiseptic additive; Benzalkonium Chloride 0.2%)

| Components | Quantity (% w/w) |
|---|---|
| Penciclovir | 1% |
| Benzalkonium Chloride | 0.2% |
| Tea Tree Oil | 1% |
| Nitrocellulose | 15% |
| Camphor | 1% |

| Components | Quantity (% w/w) |
|---|---|
| Amyl Acetate | 28% |
| Ethyl Acetate | 28% |
| Ethyl Alcohol | 15% |
| Isopropyl Alcohol | 10.8% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm Step 1: Other ingredients are mixed and dissolved separately in the following order: camphor (1.0 g), tea tree oil (1.0 g), ethyl acetate (28.0 g), Penciclovir (1.0 g), ethyl alcohol (15.0 g), isopropyl alcohol (10.8 g), and Benzalkonium (0.2 g) at room temperature with a mixing speed of 300-1000 rpm. A total mixing time including stage 1) is 60 minutes or until all the ingredients dissolve completely.

Example 10

(The liquid discreet patch with Penciclovir 1% with an antiseptic additive; Benzethonium Chloride 0.2%)

| Components | Quantity (% w/w) |
|---|---|
| Penciclovir | 1% |
| Benzethonium Chloride | 0.2% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 10.8% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Penciclovir (1.0 g), ethyl alcohol (15.0 g), isopropyl alcohol (10.8 g), and Benzethonium Chloride (0.2 g) at room temperature with a mixing speed of 300-1000 rpm. A total mixing time including stage 1) is 60 minutes or until all the ingredients dissolve completely.

Example 11

(The liquid discreet patch with Acyclovir 5%)

| Components | Quantity (% w/w) |
|---|---|
| Acyclovir | 5% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 7% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Acyclovir (5.0 g), ethyl alcohol (15.0 g), and isopropyl alcohol (7.0 g) at room temperature with a mixing speed of 300-1000 rpm. A total mixing time including stage 1) is 60 minutes or until all the ingredients dissolve completely.

Example 12

(The liquid discreet patch with Acyclovir 4.8% with an antiseptic additive; Benzethonium Chloride 0.2%)

| Components | Quantity (% w/w) |
|---|---|
| Acyclovir | 4.8% |
| Benzethonium Chloride | 0.2% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 7% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Acyclovir (4.8 g), ethyl alcohol (15.0 g), isopropyl alcohol (7.0 g), and Benzethonium Chloride (0.2 g) at room temperature with a mixing speed of 300-1000 rpm. A total mixing time including stage 1) is 60 minutes or until all the ingredients dissolve completely. A transparent solution is obtained.

Example 13

(The liquid discreet patch with Acyclovir 4.8% with an antiseptic additive; Benzalkonium Chloride 0.2%)

| Components | Quantity (% w/w) |
|---|---|
| Acyclovir | 4.8% |
| Benzalkonium Chloride | 0.2% |
| Tea Tree Oil | 1% |
| Nitrocellulose | 15% |
| Camphor | 1% |
| Amyl Acetate | 28% |
| Ethyl Acetate | 28% |
| Ethyl Alcohol | 15% |
| Isopropyl Alcohol | 7% |

Process of Preparation:
Step 1: 15.0 g of Nitrocellulose (70% dry weight: 30% isopropanol) is mixed with 28 mL of amyl acetate while stirring at room temperature for 30 minutes or until the nitrocellulose dissolves completely in amyl acetate; mixing speed is 300-1000 rpm
Step 2: Other ingredients are mixed and dissolved separately in the following order: camphor (1.0 g), tea tree oil (1.0 g), ethyl acetate (28.0 g), Acyclovir (4.8 g), ethyl alcohol (15.0 g), isopropyl alcohol (7.0 g), and Benzalkonium (0.2 g) at room temperature with a mixing speed of 300-1000 rpm. A total mixing time including stage 1) is 60 minutes or until all the ingredients dissolve completely.

Example 14

(The liquid discreet patch with Magnesium 10%)

| Components | Quantity (% w/w) |
|---|---|
| Magnesium | 10% |
| Tea Tree Oil | 1% |
| Nitrocellulose | 10% |
| Camphor | 1% |
| Amyl Acetate | 19% |
| Ethyl Acetate | 19% |
| Ethyl Alcohol | 10% |
| Dimethyl Sulfoxide | 30% |

Process of Preparation:
Step 1: 10.0 g of Nitrocellulose (70% dry weight: 30% isopropanol) is mixed with 30 mL of dimethyl sulfoxide while stirring at room temperature for 60 minutes or until the nitrocellulose dissolves completely in dimethyl sulfoxide; mixing speed is 300-1000 rpm
Step 2: Other ingredients are mixed and dissolved separately in the following order: L-Magnesium (10.0 g), ethyl alcohol (10.0 g), camphor (1.0 g), tea tree oil (1.0 g), amyl acetate (19.0 g), and ethyl acetate (19.0 g), at room temperature with a mixing speed of 300-1000 rpm. A total mixing time including stage 1) is 120 minutes or until all the ingredients dissolve completely.

Example 15

(The liquid discreet patch with Zinc 10%)

| Components | Quantity (% w/w) |
|---|---|
| Zinc | 10% |
| Tea Tree Oil | 1% |
| Nitrocellulose | 10% |
| Camphor | 1% |
| Amyl Acetate | 19% |
| Ethyl Acetate | 19% |
| Ethyl Alcohol | 10% |
| Dimethyl Sulfoxide | 30% |

Process of Preparation:
Step 1: 10.0 g of Nitrocellulose (70% dry weight: 30% isopropanol) is mixed with 30 mL of dimethyl sulfoxide while stirring at room temperature for 60 minutes or until the nitrocellulose dissolves completely in dimethyl sulfoxide; mixing speed is 300-1000 rpm
Step 2: Other ingredients are mixed and dissolved separately in the following order: L-Zinc (10.0 g), ethyl alcohol (10.0 g), camphor (1.0 g), tea tree oil (1.0 g), amyl acetate (19.0 g), and ethyl acetate (19.0 g), at room temperature with a mixing speed of 300-1000 rpm. A total mixing time including stage 1) is 120 minutes or until all the ingredients dissolve completely.

What is claimed is:

1. A formulation of a liquid discreet patch for the treatment of cold sores consisting of
   a. a translucent liquid adhesive consisting of at least one non-active ingredient and characterized in that the water content is less than 5% by weight,
   b. at least one active ingredient selected from the group consisting of Docosonol, L-Lysine, Penciclovir, and/or Acyclovir, and
   c. an anti-septic compound
   whereas, said translucent liquid adhesive is mixed with said active ingredient and applied to form a single layer whereas the formulation does not comprise a backing layer.

2. The formulation of a liquid discreet patch according to claim 1, wherein the translucent liquid adhesive consists of an alcohol base.

3. The formulation of a liquid discreet patch according to claim 1, wherein the non-active ingredient is selected from the group consisting of Nitrocellulose, Tea Tree Oil, Camphor, Dimethyl Sulfoxide (DMSO), Amyl Acetate, Ethyl Acetate, Ethyl Alcohol and Isopropyl Alcohol.

4. The formulation of a liquid discreet patch according to claim 1, wherein the active ingredient consists of at least one of Docosanol and L-lysine.

5. The formulation of a liquid discreet patch according to claim 1, wherein the anti-septic compound is selected from the group consisting of Benzalkonium Chloride and Benzethonium Chloride.

6. The formulation of a liquid discreet patch according to claim 1, wherein the active ingredient consists of Docosanol 4% by weight, and the adhesive consists of Tea Tree Oil 1% by weight, Nitrocellulose 15% by weight, Camphor 1% by weight, Amyl Acetate 28% by weight, Ethyl Acetate 28% by weight, Ethyl Alcohol 15% by weight and Isopropyl Alcohol 8% by weight.

7. The formulation of a liquid discreet patch according to claim 1, wherein the active ingredient consists of Docosanol 4% by weight, and the adhesive consists of Tea Tree Oil 1% by weight, Nitrocellulose 15% by weight, Camphor 1% by weight, Amyl Acetate 28% by weight, Ethyl Acetate 28% by weight, Ethyl Alcohol 15% by weight, Isopropyl Alcohol 8% by weight and Benzethonium Chloride 0.2% by weight.

8. The formulation of a liquid discreet patch according to claim 1, wherein the active ingredient consists of L-lysine 10% by weight, and the adhesive consists of Tea Tree Oil 1% by weight, Nitrocellulose 10% by weight, Camphor 1° A) by weight, Amyl Acetate 19% by weight, Ethyl Acetate 19% by weight, Ethyl Alcohol 10% by weight and Dimethyl Sulfoxide 30% by weight.

9. The formulation of a liquid discreet patch according to claim 1, wherein the active ingredient consists of Docosanol 4% by weight and L-lysine 6% by weight, and the adhesive consists of Tea Tree Oil 1% by weight, Nitrocellulose 10% by weight, Camphor 1% by weight, Amyl Acetate 19% by weight, Ethyl Acetate 19% by weight, Ethyl Alcohol 10% by weight and Dimethyl Sulfoxide 30% by weight.

10. The formulation of a liquid discreet patch according to the claim 1, wherein the active ingredient consists of Penciclovir 1% by weight, and the adhesive consists of Tea Tree Oil 1% by weight, Nitrocellulose 15% by weight, Camphor 1% by weight, Amyl Acetate 28% by weight, Ethyl Acetate 28% by weight, Ethyl Alcohol 15% by weight and Isopropyl Alcohol 11% by weight.

11. The formulation of a liquid discreet patch according to claim 1, wherein the active ingredient consists of Acyclovir 5% by weight, and the adhesive consists of Tea Tree Oil 1% by weight, Nitrocellulose 15% by weight, Camphor 1% by weight, Amyl Acetate 28% by weight, Ethyl Acetate 28% by weight, Ethyl Alcohol 15% by weight and Isopropyl Alcohol 7% by weight.

12. A method of use of a liquid discreet patch of claim 1, the method comprising:
   (a) positioning the liquid discreet patch on to a lesion surface and maintaining contact between the liquid discreet patch with the lesion surface for at least 2 hours, but no longer than 12 hours, and
   (b) delivering subsequent patches and maintaining said subsequent patches in contact with the lesion surface, until such time as re-epithelialization of the lesion surface is completed.

13. The formulation of a liquid discreet patch according to claim 1, wherein the liquid discreet patch is characterized by being applied as a liquid and once dried, forming a translucent film barrier with a thickness of between 5 and 1300 microns.

14. The formulation of a liquid discreet patch according to claim 1, wherein the liquid discreet patch is characterized as being flexible and porous with the ability to allow moisture to pass through and evaporate, maintaining a dry surface that is unaffected by movement in regular wear.

\* \* \* \* \*